United States Patent [19]

Dohrer et al.

[11] Patent Number: 4,680,328

[45] Date of Patent: Jul. 14, 1987

[54] INSECT RESISTANT POLYETHYLENE COMPOSITION SUITABLE FOR WIRE AND CABLE APPLICATIONS

[75] Inventors: Gregory L. Dohrer, Clute; George W. Knight, Lake Jackson, both of Tex.

[73] Assignee: The Dow Chemical Company, Midland, Mich.

[21] Appl. No.: 806,904

[22] Filed: Dec. 9, 1985

Related U.S. Application Data

[63] Continuation-in-part of Ser. No. 676,341, Nov. 29, 1984, abandoned.

[51] Int. Cl.$^4$ .............................................. C08K 5/53
[52] U.S. Cl. .................................... 524/137; 523/122; 524/515; 524/523
[58] Field of Search ................... 524/137, 515, 523; 523/122

[56] References Cited

U.S. PATENT DOCUMENTS

| | | | |
|---|---|---|---|
| 3,212,967 | 10/1965 | McFadden | 167/42 |
| 3,318,769 | 5/1967 | Folckemer | 167/42 |
| 3,400,093 | 9/1968 | Feinberg | 260/29.6 |
| 3,408,323 | 10/1968 | Hackney | 260/45.85 |
| 4,065,555 | 12/1977 | Potter | 424/83 |
| 4,237,113 | 12/1980 | Cardarelli | 424/78 |
| 4,350,678 | 9/1982 | Palvarini | 424/27 |

FOREIGN PATENT DOCUMENTS

| | | |
|---|---|---|
| 1480125 | 7/1977 | United Kingdom . |
| 1538222 | 1/1979 | United Kingdom . |

Primary Examiner—Joseph L. Schofer
Assistant Examiner—J. M. Reddick
Attorney, Agent, or Firm—W. J. Lee; D. N. Lundeen

[57] ABSTRACT

An insect-resistant composition containing at least about 75 percent by weight of a polyethylene, e.g. LDPE, HDPE, or LLDPE, at least about 5 percent by weight, up to an amount approaching about 25 percent by weight of a compatability additive selected from chlorinated polyethylene and ethylene-n-butyl acrylate copolymer, and an insecticidally effective amount, up to about 8 weight percent, of an insecticide, e.g. halopyridyl phosphates. Optionally, the compatibility additive may include carbon black in an amount of about 0.5–7.5 percent by weight of the composition. The composition has utility in being formed into useful articles, especially in wire and cable applications, which are insect resistant substantially for the useful life of the articles.

19 Claims, No Drawings

4,680,328

INSECT RESISTANT POLYETHYLENE COMPOSITION SUITABLE FOR WIRE AND CABLE APPLICATIONS

CROSS REFERENCE TO RELATED APPLICATION

This application is a continuation-in-part of our application Ser. No. 676,341, filed Nov. 29, 1984, now abandoned.

FIELD OF THE INVENTION

This invention relates to a polyethylene composition containing an insecticide, and more particularly, to such compositions which can be formed into useful products which are resistant to insect attack over the useful lifetime of the formed product.

BACKGROUND OF THE INVENTION

Polymeric insecticidal compositions in the form of pellets, granules or film have been widely used as a means of providing a slow release, long term insecticide formulation which kills insects contacting or coming within close proximity of the pellets, granules or film. Such formulations are widely used in agricultural and domestic applications by spreading or distributing the pellets, granules or film containing the insecticide in the area to be protected. Generally, these formulations are designed so that insecticide therein gradually diffuses to the surface of the polymer so that it will be transmitted to an insect coming into contact or close proximity therewith. Thus, over a period of time, the insecticide is released from the formulation until the pellets, granules or film is no longer effective in killing insects and must be replaced. Typically, the reported useful retention time of the insecticide ranges from a month to two or three years at the most.

In many instances, it is desirable to form useful articles from a thermoplastic composition. In certain applications, however, these useful articles are subject to insect attack and it is, therefore, desired that such articles have resistance to attack from insects. For example, in electrical wiring installations, nonresistant junction boxes and cable jackets are frequently invaded by ants or crickets, creating fire and safety hazards to personnel, often interrupting electrical service, and necessitating replacement of the junction box or cable. Also, nonresistant tubing in drip irrigation systems which has been damaged by ants, for example, results in improper distribution of water, wasting water and often damaging crops, as well as necessitating replacement of the tubing.

In manufacturing useful articles which are insect resistant, the insecticidal thermoplastic compositions heretofore known have been of limited utility. Because of the diffusion of the insecticide from the thermoplastic composition, it has heretofore been necessary to incorporate as high a percentage of the insecticide in the polymer as is possible without phase separation or insecticide exudation in order to extend the insecticide retention time thereof. In most systems, however, the maximum insecticide concentration has been quite low, for example, 1.8-2 weight percent in the polyethylenehalopyridyl phosphate system. Moreover, the high content of the insecticide has adversely affected the desirable physical properties of the composition. These adversely affected properties include those desirable for end use as useful articles, such as resistance to creep and stress crack, tensile strength, yield strength and elongation, and those necessary for processability. On the other hand, if the insecticide content is reduced to the extent that the physical properties of the polymer are not adversely affected, the retention time of the insecticide is correspondingly decreased so that useful articles formed from the thermoplastic composition lose their resistance to insect attack long before the useful lifetime of the article has expired. Thus, when formed from the heretofore known thermoplastic insecticidal compositions, articles such as electrical junction boxes, jackets for electrical cables, and tubing for drip irrigation which are subjected to insect attack after losing resistance thereto must be replaced substantially prior to expiration of the useful life thereof which would normally be expected in the absence of such insect attack.

SUMMARY OF THE INVENTION

In contrast to the heretofore known insecticidal polymeric compositions, the present invention provides an insecticide-containing polyethylene composition with an improved ability to accept higher concentrations of insecticide, markedly improved long term retention of insecticide, and, in addition, has the physical properties desirable for end use as a useful article and necessary for processing into such articles. The insecticide-containing polyethylene composition of the invention can be formed into useful articles which are resistant to attack from insects substantially for the entire expected life of the article.

Briefly, the present invention is an insect-resistant polyethylene composition suitable for forming into and use as electrical cable jacketing, electrical junction boxes or drip irrigation tubing, and having resistance to attack from insects for an extended period of time, consisting essentially of: (a) at least about 75 weight percent, preferably 75–85 weight percent, of a polyethylene selected from the group consisting of low density polyethylene high density polyethylene, and linear low density polyethylene; (b) at least about 5 weight percent, up to an amount approaching 25 weight percent, preferably 10-20 weight percent, of a compatibility additive selected from the group consisting of chlorinated polyethylene and ethylene-n-butyl acrylate copolymer; and (c) an insecticidally effective amount up to about 8 weight percent, preferably from about 3 to about 6 weight percent, of an insecticide. The invention is more fully explained in the detailed description and examples which follow.

DETAILED DESCRIPTION OF THE PREFERRED EMBODIMENTS

The composition of the present invention consists essentially of polyethylene, compatibility additive and insecticide in such proportions to substantially retain the physical properties of the polyethylene and to have an extended retention of the insecticide.

The composition must contain at least about 75 percent by weight of the polyethylene. If less than this amount is employed, the physical properties of the composition will be adversely affected. Preferably, the composition contains from about 75 to about 85 percent by weight of the polyethylene. In addition, the polyethylene may comprise only one polyethylene or type of polyethylene, or it may be a blend of two or more polyethylenes of the same or different type, depending on the desired end use. For example, in some applications it may be desirable to employ a blend of both high and low density polyethylene.

The polyethylenes suitable for use in the composition of the invention include low density polyethylene (LDPE), high density polyethylene (HDPE) and linear low density polyethylene (LLDPE). The polyethylene may have a melt index in the range of from about 0.01 to about 100 and density in the range of from about 0.900 to about 0.975 g/cc. Preferably, the polyethylene has a melt index of about 0.05–50 and a density of about 0.915–0.960 g/cc. As used herein, melt index in reference to polyethylene, and melt flow value, in reference to copolymers, are determined according to ASTM D-1238 condition E (190° C./2.16 kg). The exact properties of the polyethylene will depend on the specific end use to which it is to be applied.

The polyethylenes (LDPE, HDPE and LLDPE) are very well known. Low density polyethylenes are generally prepared at high temperature and pressure with a free radical initiator such as a peroxide. These LDPE polymers contain branched chains of polymerized monomer units pendent from the main polymer "backbone" and generally have densities in the range of about 0.910–0.935 g/cc.

The HDPE polymers are prepared with coordination catalysts of the "Ziegler" type or "Phillips" type including variations of the Ziegler type, such as the Natta type. These catalysts may be used at high pressures, but may also be (and generally are) used at low or intermediate pressures. The products made by these catalysts are generally known as linear polymers because of the substantial absence of branched chains of polymerized monomer units pendent from the main polymer backbone. Linear polyethylene (HDPE) ordinarily has a density in the range of about 0.941–0.965 g/cc.

LLDPE is also prepared with coordination catalysts. Generally, LLDPE is obtained by polymerizing ethylene along with minor amounts of an $\alpha$-olefin having from 3 to 12 carbon atoms, typically 4 to 8. The amount of the $\alpha$-olefin comonomer (typically 1–10 wt.%) is generally sufficient to cause the density of the polymer to be substantially in the same density range as LDPE, due to the alkyl side chains on the polymer molecule (typically 5–15 alkyl side chains per 1000 carbon atoms in the linear backbone), yet the polymer remains in the linear classification. These LLDPE polymers retain much of the strength, crystallinity and toughness normally found in HDPE.

The composition of the invention also contains from about 5 to about 25 weight percent of a compatibility additive. Preferably, the composition comprises from about 10 to about 20 weight percent of the compatibility additive. Since the composition must contain at least about 75 weight percent of the base thermoplastic polymer, preferably 75–85 weight percent, it is readily appreciated that when the composition contains an insecticidally effective amount of an insecticide which is considerably less than 1 weight percent of the composition, the term "about" in reference to a maximum weight percentage of compatibility additive will mean less than the specified percentage, and not exactly or more than the specified percentage. In this and other cases, it will be understood that the sum of the weight percentages of the base thermoplastic polymer, compatibility additive and insecticide must not be more than 100.

Suitable compatibility additives include chlorinated polyethylene (CPE) containing from about 10 to about 50 percent by weight chlorine, ethylene-n-butyl acrylate copolymers (EnBA) containing from about 10 to about 50 weight percent n-butyl acrylate, and combinations thereof. The CPE may have a viscosity of from about 5,000 to about 40,000 Pa-s, preferably about 6,000–28,000 Pa-s, measured at 190° C. and a shear rate of 145/sec. The preferred CPE has a chlorine content of about 35 percent by weight.

The EnBA may contain from about 10 to about 50 percent by weight n-butyl acrylate, preferably from about 25 to about 50 percent by weight, and may have a melt flow value of from about 0.5 to about 2000, preferably from about 1.0 to about 1500, and more preferably from about 1100 to about 1300.

In an especially preferred embodiment, the compatibility additive is a combination of the aforesaid chlorinated polyethylene and ethylene-n-butyl acrylate copolymer. This combination is most effective when the chlorinated polyethylene and ethylene-n-butyl acrylate copolymer are present in approximately equal amounts.

Optionally, the compatibility additive may include carbon black, present in the composition of the invention in an amount ranging from about 0.5 to about 7.5 weight percent of the composition, preferably from about 2 to about 4 weight percent of the composition. Suitable carbon blacks include furnace and channel carbon blacks.

The particular insecticide used in the invention is not believed to be particularly critical, as long as it does not adversely affect the properties of the composition when the insecticide is present in an insecticidally effective amount. By the term "insecticidally effective" is meant utility for inhibiting, repelling, exterminating or otherwise altering the normal activities of insects. Preferably, the particular insecticide used is substantially stable during conditions of preparation and use of the composition and not substantially subject to chemical decomposition. Particularly useful insecticides are the O-halopyridyl phosphates including O-halopyridyl phosphorothioates described in U.S. Pat. No. 3,244,586. As used herein, the term "halopyridyl phosphates" will be used to mean the class of compounds disclosed and claimed in U.S. Pat. No. 3,244,586. Particularly desirable halopyridyl phosphates include O,O-diethyl-O-3,5,6-trichloro-2-pyridyl phosphorothioate and O,O-dimethyl-O-3,5,6-trichloro-2-pyridyl phosphorothiate. Other contemplated insecticides include 4-diethylamino-3,5-xylyl methylcarbonate, 2-(1-methylethoxy)phenol methylcarbamate, 4-t-butyl-2-chlorophenyl methyl methylphosphoamidate, O,O-diethyl-O-4-t-butylthio-2-methylphenyl phosphorothioate, O,O-diethyl-O-(4-nitrophenyl)phosphorotioate, O,O-diethyl-O-(2-isopropyl-6-methyl-5-pyrimidinyl)phosphorothioate, and 2,2-dichlorovinyldimethyl phosphate. Such insecticides and the methods for preparing them are well known.

The composition must contain the insecticide in at least an amount which is insecticidally effective. In the case of the halopyridyl phosphates, this amount may be as little as 0.01 weight percent of the composition. In applications in which long-term insect resistance is required, however, it will be desirable to incorporate as much insecticide into the composition as is feasible. With the composition of the invention, it is possible to incorporate insecticide therein in a proportion up to about 8 weight percent of the composition without the occurrence of phase separation or insecticide exudation. In applications in which the physical properties of the composition are a critical consideration, it is preferred that the composition contain the insecticide in a proportion of from about 3 to about 6 weight percent, more preferably about 5 weight percent.

In addition, the composition may contain additional additives such as, for example, colorants, pigments, antioxidants, heat and light stabilizers, or fillers such as silica, calcium carbonate, metal oxides, talc, clay, sawdust, rice hulls, wood, flour, starch, ground bark or the like. Such additives do not adversely affect the retention of the insecticide in the composition, and are employed in relatively minor amounts to avoid substantially adversely affecting the physical properties of the composition. When such additional additives are present in the composition, they are to be excluded from determinations of the weight percentages of polyethylene, compatibility additive and insecticide employed in the composition of the invention.

In preparing the composition of the invention, the polyethylene and compatibility additive may be blended in any conventional manner with conventional polymer blending apparatus, such as, for example, roll mills, Banbury mixers and extruders. The insecticide may be added during melt blending of the polyethylene and the compatibility additive, or by absorption of the insecticide in the polyethylene, compatibility additive or blend thereof as described in U.K. Patent Specification No. 1,480,125. The composition should be sufficiently mixed to insure uniform distribution of the compatibility additive and the insecticide. Preferably, the insect-resistant composition is first formed into pellets or other forms which can be subsequently processed into useful articles by, for example, injection molding, blow molding, rotational molding or extrusion. Specific representative examples of such useful articles include jackets for electrical cables, electrical junction boxes, and tubing for drip irrigation.

The following examples illustrate the long-term retention of insecticide in the thermoplastic composition of the invention.

EXAMPLES 1–4

A low density polyethylene having a density of 0.920 g/cc and a melt index of 0.2 and any compatibility additive was put on a two-roll mill and fluxed until molten. O,O-diethyl-O-3,5,6-trichloro-2-pyridyl phosphorothioate was then added to the molten polymer and the mixture was run through the mill 3–4 times to ensure uniform distribution of the compatibility additive and insecticide. The mixture was chopped when removed from the mill and molded into a 3.2 mm test plaque using a heated press. The examples had compositions as presented in Table I.

TABLE I

| Example No. | Composition (wt. %) | | | | |
|---|---|---|---|---|---|
| | LDPE[1] | Insecticide[2] | E-nBA[3] | CPE[4] | CB[5] |
| 1 | 99 | 1 | | | |
| 2 | 89 | 1 | 10 | | |
| 3 | 86.4 | 1 | 10 | | 2.6 |
| 4 | 79 | 1 | 10 | 10 | |

[1] Low density polyethylene, density .920, melt index 0.2
[2] O,O-Diethyl-O-3,5,6-Trichloro-2-pyridyl phosphorothioate
[3] Ethylene-n-butyl acrylate copolymer, 37.5 wt. % nBA, melt flow value 1200.
[4] Chlorinated high density polyethylene, 35.6 wt. % chlorine, viscosity 7280 Pa-s at a shear rate of 145/sec and a temperature of 190° C.
[5] Carbon black obtained from Cabot Corp. under the designation VULCAN 9

The samples were evaluated for insecticide retention by aging in an oven at 70° C. for 672 hours. The estimated aging time at 70° C., and at 25° C., required for the insecticide concentration to fall below 0.01 weight percent was calculated by determining the best-fit exponential extinction coefficients and extrapolating. The results are listed in Table II.

TABLE II

| Example No. | Insecticide Retention After 672 hrs at 70° C., % of Initial | Estimated Retention Time at 70° C. to 0.01 wt. % Insecticide, hrs | Estimated Rention Time at 25° C. to 0.01 wt. % Insecticide, yrs |
|---|---|---|---|
| 1 | 12.5 | 3154 | 10.5 |
| 2 | 33.8 | 6132 | 20.3 |
| 3 | 44.1 | 9110 | 30.2 |
| 4 | 54.1 | 12790 | 42.4 |

The above examples demonstrate that an effective amount of insecticide is retained in the composition for a period of time substantially exceeding that of the composition containing no compatibility additive and that reported for heretofore known compositions.

The following examples illustrate that the composition of the invention, quite surprisingly, has the physical properties desirable for end use as useful articles and processing into useful articles.

EXAMPLES 5–7

Various blends of polyethylenes and compatibility additives were prepared by dry blending and extrusion. To one blend, insecticide was added by absorption. The compositions are presented in Table III.

TABLE III

| Example No. | Composition (wt. %) | | | | |
|---|---|---|---|---|---|
| | HDPE[6] | LLDPE[7] | Insecticide[8] | CPE[9] | CB[10] |
| 5 | 37.0 | 60.4 | — | — | 2.6 |
| 6 | 29.5 | 58.4 | — | 10.5 | 1.6 |
| 7 | 28.0 | 55.5 | 5.0 | 10.0 | 1.5 |

[6] High Density polyethylene, density 0.960, melt index 0.9.
[7] Linear low density polyethylene, density 0.920, melt index 1.0.
[8] O,O-Diethyl-0-3,5,6-trichloro-2-pyridyl phosphorothiate.
[9] Chlorinated high density polyethylene 35.6 wt. % chlorine, viscosity 7820 Pa-s at a shear rate of 145/sec and a temperature of 190° C.
[10] Carbon black obtained from Cabot Corp. under the designation VULCAN 9.

The compositions were then evaluated for physical properties according to the procedures in the U.S. Department of Agriculture, Rural Electrification Administration Specification PE-200, Appendix F. The results are presented in Table IV.

TABLE IV

| Example No. | Stress Crack Resistance | Tensile Strength (MPa) | Yield Strength (MPa) | Ultimate Elongation (%) |
|---|---|---|---|---|
| 5 | 0/24 | 30.8 | 13.4 | 850 |
| 6 | 0/24 | 27.2 | 14.4 | 920 |
| 7 | 0/24 | 20.7 | 10.4 | 850 |

[11] Based on a test commonly known as the Bell Bent Strip Test, reported as number of failures/hours of test.

The above examples demonstrate the minimal effect of the compatibility additive on the physical properties of the base thermoplastic polymer. Note that there is no difference in either the stress crack resistance or ultimate elongation between Example 5, containing only polyethylene and carbon black, and Example 7, containing polyethylene, compatibility additives, and insecticide. While there is a reduction in tensile strength and yield strength, the reduction is minimal and does not affect the physical performance characteristics or manufactured article adversely to a significant extent. The composition of Example 7 met the specification of the U.S. Department of Agriculture, Rural Electrification Administration Specification PE-200. Also, drip tubes made from the composition of Example 7 were suitable for use in irrigation systems.

Having described our insect-resistant polyethylene composition above, many variations in the particular materials used, ratios thereof, and methods of preparation, as well as in the illustrated details, will occur to those skilled in the art. It is intended that all such variations which fall within the scope and spirit of the appended claims be embraced thereby.

What is claimed is:

1. A composition suitable for forming into and use as electrical cable jacketing, electrical junction boxes or drip irrigation tubing, and having resistance to attack from insects for an extended period of time, consisting essentially of:
   (a) at least about 75 weight percent polyethylene having a melt index from about 0.01 to about 100 and a density from about 0.900 to about 0.975 g/cc, said polyethylene selected from the group consisting of low density polyethylene, high density polyethylene, linear low density polyethylene, and combinations thereof;
   (b) from about 5 to about 25 weight percent of a compatibility additive selected from the group consisting of: chlorinated polyethylenes containing from about 10 to about 50 percent by weight chlorine and having a viscosity of about 5,000–40,000 Pa-s at 190° C. and a shear rate of 145/sec.; ethylene-n-butyl acrylate copolymers having a melt flow value of about 0.5–2000 and containing from about 10 to about 50 weight percent n-butyl acrylate; and combinations thereof; and
   (c) an insecticidally effective amount, up to about 8 weight percent of an insecticide selected from halopyridyl phosphates.

2. The composition of claim 1, wherein said composition comprises from about 75 to about 85 percent by weight of said polyethylene.

3. The composition of claim 1, wherein said composition comprises from about 10 to about 20 percent by weight of said compatibility additive.

4. The composition of claim 1, wherein said compatibility additive further includes carbon black in an amount of from about 0.5 to about 7.5 percent by weight of said composition.

5. The composition of claim 1, wherein said composition contains from about 3 to about 6 percent by weight of said insecticide.

6. The composition of claim 1, wherein said insecticide is O,O-diethyl-O-3,5,6-trichloro-2-pyridyl phosphorothioate.

7. The composition of claim 1, wherein said insecticide is O,O-dimethyl-O-3,5,6-trichloro-2-pyridyl phosphorothioate.

8. The composition of claim 1, wherein said polyethylene has a melt index of from about 0.05 to about 50 and a density of from about 0.915 to about 0.960 g/cc.

9. The composition of claim 1, wherein said compatibility additives is selected from the group consisting of: (i) chlorinated polyethylene containing from about 10 to about 50 percent by weight chlorine and having a viscosity of about 6,000–28,000 poise at 190° C., and a shear rate of 145/sec.; (ii) ethylene-n-butyl acrylate copolymer containing from about 25 to about 50 percent by weight n-butyl acrylate and having a melt flow value of from about 1 to about 1500; and combinations thereof.

10. A composition suitable for forming into and use as electrical cable jackets, electrical junction boxes or drip irrigation tubing, and having resistance to attack from insects for an extended period of time, consisting essentially of:
   (a) from about 75 to about 85 weight percent polyethylene having a melt index of from about 0.5 to about 50 and a density of from about 0.915 to about 0.960 g/cc, said polyethylene selected from the group consisting of: low density polyethylene, high density polyethylene, linear low density polyethylene, and combinations thereof;
   (b) from about 10 to about 20 weight percent of a compatibility additive selected from the group consisting of:
      (i) chlorinated polyethylene containing from about 10 to about 50 percent by weight chlorine and having a viscosity of from about 6,000 to about 28,000 poise at 190° C. and a shear rate of 145/sec;
      (ii) ethylene-n-butyl acrylate copolymer containing from about 25 to about 50 percent by weight n-butyl acrylate and having a melt flow value of from about 1 to about 1500; and
      (iii) combinations thereof; and
   (c) from about 3 to about 6 weight percent of halopyridyl phosphate.

11. The composition of claim 10, wherein said chlorinated polyethylene contains about 35 weight percent chlorine.

12. The composition of claim 10, wherein said ethylene-n-butyl acrylate copolymer has a melt flow value of from about 1100 to about 1300.

13. The composition of claim 10, wherein said compatibility additive further includes carbon black in an amount of from about 2 to about 4 percent by weight of said composition.

14. The composition of claim 10, wherein said halopyridyl phosphate is O,O-diethyl-3,5,6-trichloro-2-pyridyl phosphorothioate.

15. The composition of claim 10, wherein said halopyridyl phosphate is O,O-dimethyl-3,5,6-trichloro-2-pyridyl phosphorothioate.

16. The composition of claim 10, wherein said polyethylene is low density polyethylene.

17. The composition of claim 10, wherein said polyethylene is high density polyethylene.

18. The composition of claim 10, wherein said polyethylene is linear low density polyethylene.

19. A composition suitable for forming into and use as electrical cable jacketing, electrical junction boxes or drip irrigation tubing, and having resistant to attack from insects for an extended period of time, consisting essentially of:
   (a) from about 75 to about 85 weight percent polyethylene having a melt index of from about 0.05 to about 50, a density of from about 0.915 to about 0.960 g/cc, and selected from the group consisting of low density polyethylene, high density polyethylene, linear low density polyethylene, and combinations thereof;
   (b) from about 10 to about 20 weight percent of a compatibility additive consisting essentially of:
      (i) chlorinated polyethylene containing about 35 percent chlorine and having a viscosity of from about 6000 to about 28,000 poise at 190° C. and a shear rate of 145/sec.;

(ii) ethylene-n-butyl acrylate copolymer containing from about 25 to about 50 percent by weight n-butyl acrylate and having a melt flow value of from about 1100 to about 1300; and (iii) carbon black in an amount of from about 2 to about 4 percent by weight of the composition; and (c) about 5 weight percent of an insecticide selected from the group consisting of: O,O-diethyl-3,5,6-trichloro-2-pyridyl phosphorothioate and O,O-dimethyl-3,5,6-trichloro-2-pyridyl phosphorothioate.

* * * * *

UNITED STATES PATENT AND TRADEMARK OFFICE
CERTIFICATE OF CORRECTION

PATENT NO. : 4,680,328

DATED : July 14, 1987

INVENTOR(S) : Gregory L. Dohrer & George W. Knight

It is certified that error appears in the above-identified patent and that said Letters Patent is hereby corrected as shown below:

On the cover page under the heading Abstract, about line 5, "compatability" should read --compatibility--.

Col. 4, line 52, "phosphorotioate," should read --phosphorothioate,--.

Col. 6, line 7, Table II in the fourth column, "Rention" should read --Retention--.

Col. 6, Table III in footnote number 8, "phosphorothiate." should read --phosphorothioate.--.

Col. 6, Table IV in the second column, "Stress Crack Resistance" should read --Stress Crack Resistance11--.

Col. 7, line 63, "additives" should read --additive--.

Col. 8, line 5, "jackets," should read --jacketing,--.

Col. 8, line 55, "resistant" should read --resistance--.

Signed and Sealed this

Fifth Day of January, 1988

Attest:

DONALD J. QUIGG

*Attesting Officer*     *Commissioner of Patents and Trademarks*